(12) United States Patent
Lennartz et al.

(10) Patent No.: US 11,903,635 B2
(45) Date of Patent: Feb. 20, 2024

(54) ELECTROSURGICAL FORCEPS INCLUDING TISSUE INDICATION

(71) Applicant: Covidien LP, Mansfield, MA (US)

(72) Inventors: Amanda H. Lennartz, Erie, CO (US); Daniel A. Joseph, Golden, CO (US); Jennifer R. Mchenry, Denver, CO (US); Cornelia F. Twomey, Longmont, CO (US); Erin E. Wehrly, Longmont, CO (US); Pierre Gherardi, Longmont, CO (US); David M. Garrison, Longmont, CO (US); Tyler J. Bagrosky, Arvada, CO (US); Jing Zhao, Superior, CO (US)

(73) Assignee: Covidien LP, Mansfield, MA (US)

( * ) Notice: Subject to any disclaimer, the term of this patent is extended or adjusted under 35 U.S.C. 154(b) by 353 days.

(21) Appl. No.: 17/186,599

(22) Filed: Feb. 26, 2021

(65) Prior Publication Data
US 2021/0267664 A1  Sep. 2, 2021

Related U.S. Application Data

(60) Provisional application No. 62/983,371, filed on Feb. 28, 2020.

(51) Int. Cl.
*A61B 18/14* (2006.01)
*A61B 18/00* (2006.01)

(52) U.S. Cl.
CPC ............... *A61B 18/1445* (2013.01); *A61B 2018/0091* (2013.01); *A61B 2018/00773* (2013.01)

(58) Field of Classification Search
CPC ...... A61B 18/1445; A61B 2018/00773; A61B 2018/0091
See application file for complete search history.

(56) References Cited

U.S. PATENT DOCUMENTS

| | | |
|---|---|---|
| 5,851,180 A | 12/1998 | Crosby et al. |
| 8,382,754 B2 | 2/2013 | Odom et al. |
| 8,469,956 B2 | 6/2013 | McKenna et al. |
| 8,764,749 B2 | 7/2014 | McKenna et al. |
| 8,845,665 B2 | 9/2014 | Whitman |
| 9,113,905 B2 | 8/2015 | McKenna et al. |
| 9,247,988 B2 | 2/2016 | McKenna et al. |
| 9,301,691 B2 | 4/2016 | Hufnagel et al. |

(Continued)

*Primary Examiner* — Thomas A Giuliani
*Assistant Examiner* — Ryan T Clark
(74) *Attorney, Agent, or Firm* — Carter, DeLuca & Farrell LLP

(57) ABSTRACT

An electrosurgical system includes an end effector assembly, a display, and a controller. The end effector assembly includes first and second jaw members each defining a tissue-treating surface. At least one of the first or second jaw members is movable relative to the other between a spaced-apart position and an approximated position for grasping tissue between the tissue-treating surfaces thereof. At least one of the first or second jaw members includes a sensor. The controller is configured to receive sensor data from the sensor, generate a tissue indication based upon the sensor data, and output the tissue indication to the display. The display is configured to display the tissue indication. The tissue indication indicates a location along the first jaw member at which tissue is grasped between the tissue-treating surfaces of the first and second jaw members.

20 Claims, 7 Drawing Sheets

(56) References Cited

U.S. PATENT DOCUMENTS

| | | | |
|---|---|---|---|
| 9,474,570 B2 | 10/2016 | McKenna et al. | |
| 9,662,514 B2 | 5/2017 | Whitman | |
| 9,913,644 B2 | 3/2018 | McCuen | |
| 10,117,705 B2 | 11/2018 | Chernov et al. | |
| 10,130,413 B2 | 11/2018 | Brandt et al. | |
| 10,245,104 B2 | 4/2019 | McKenna et al. | |
| 10,258,359 B2 | 4/2019 | Kapadia | |
| 2007/0173811 A1* | 7/2007 | Couture | A61B 18/1445 606/45 |
| 2011/0251605 A1* | 10/2011 | Hoarau | A61B 5/4875 606/41 |
| 2012/0296205 A1* | 11/2012 | Chernov | A61B 18/1445 600/431 |
| 2012/0296238 A1 | 11/2012 | Chernov et al. | |
| 2015/0223868 A1 | 8/2015 | Brandt et al. | |
| 2016/0206209 A1 | 7/2016 | Hufnagel et al. | |
| 2017/0079740 A1 | 3/2017 | Hufnagel et al. | |
| 2017/0215944 A1 | 8/2017 | Keffeler | |
| 2017/0238991 A1* | 8/2017 | Worrell | H05K 3/0011 |
| 2017/0319266 A1 | 11/2017 | Roy et al. | |

\* cited by examiner

ELECTROSURGICAL FORCEPS INCLUDING TISSUE INDICATION

CROSS-REFERENCE TO RELATED APPLICATIONS

This application claims the benefit of, and priority to, U.S. Provisional Patent Application No. 62/983,371, filed on Feb. 28, 2020, the entire contents of which are hereby incorporated herein by reference.

FIELD

The present disclosure relates to electrosurgical instruments and, more particularly, to electrosurgical forceps including tissue indications to facilitate treating and/or cutting tissue.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife or cutting member utilized to effectively sever the treated tissue.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is an electrosurgical system including an end effector assembly, a display, and a controller. The end effector assembly includes first and second jaw members each defining a tissue-treating surface. At least one of the first or second jaw members is movable relative to the other between a spaced-apart position and an approximated position for grasping tissue between the tissue-treating surfaces thereof. At least one of the first or second jaw members includes a sensor. The controller is configured to receive sensor data from the sensor, generate a tissue indication based upon the sensor data, and output the tissue indication to the display. The display is configured to display the tissue indication. The tissue indication indicates a location along, e.g., a length and/or width, of the first jaw member and/or the second jaw member at which tissue is grasped between the tissue-treating surfaces of the first and second jaw members.

In an aspect of the present disclosure, the display is an integrated display incorporated into the first jaw member and viewable from an exterior-facing surface thereof. In such aspects, the tissue indication is displayed on the integrated display.

In another aspect of the present disclosure, the display is configured to project the tissue indication, virtually or physically, onto an exterior-facing surface of the first jaw member.

In another aspect of the present disclosure, the display is a surgical display configured to display a video image of a surgical site. In such aspects, the display is configured to overlay the tissue indication, virtually, on an image of an exterior-facing surface of the first jaw member displayed on the surgical display.

In still another aspect of the present disclosure, the tissue indication is further configured to indicate a size, e.g., width, length, and/or thickness, of tissue grasped between the tissue-treating surfaces of the first and second jaw members relative to a size e.g., width, length, and/or thickness, of the first and/or second jaw member. The relative comparison may be indicated visually, via mathematical ratios, and/or in other suitable manners.

In yet another aspect of the present disclosure, the sensor includes at least one pressure-sensitive resistive panel, e.g., to sense pressure information. Alternatively, the sensor includes an elastomeric contact sensor, e.g., to sense texture information.

In still yet another aspect of the present disclosure, the electrosurgical instrument further includes a housing with a shaft extending distally from the housing. The end effector assembly is disposed at a distal end portion of the shaft. A manual actuator, e.g., handle, may be coupled to the housing and configured to move the at least one of the first or second jaw members between the spaced-apart position and the approximated position.

In another aspect of the present disclosure, the electrosurgical instrument further includes first and second shaft members pivotably coupled to one another about a pivot. The end effector assembly, in such aspects, extends distally from the pivot and the first and second shaft members are movable relative to one another to move the at least one of the first or second jaw members between the spaced-apart position and the approximated position.

In another aspect of the present disclosure, the electrosurgical instrument further includes a robotic arm with the end effector assembly extending distally from the robotic arm.

Another electrosurgical system provided in accordance with the present disclosure includes an end effector assembly including first and second jaw members each defining a tissue-treating surface. At least one of the first or second jaw members is movable relative to the other between a spaced-apart position and an approximated position for grasping tissue between the tissue-treating surfaces thereof. At least one of the first or second jaw members includes a contact sensor. A controller is configured to receive sensor data from the contact sensor indicating a texture of tissue grasped between the first and second jaw members, and to determine at least one of a type of tissue, a state of tissue, or the presence of a foreign object or a critical tissue based upon the sensor data.

In an aspect of the present disclosure, the contact sensor is an elastomeric contact sensor.

The electrosurgical instrument may additionally include any or all of the features detailed above or otherwise herein.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
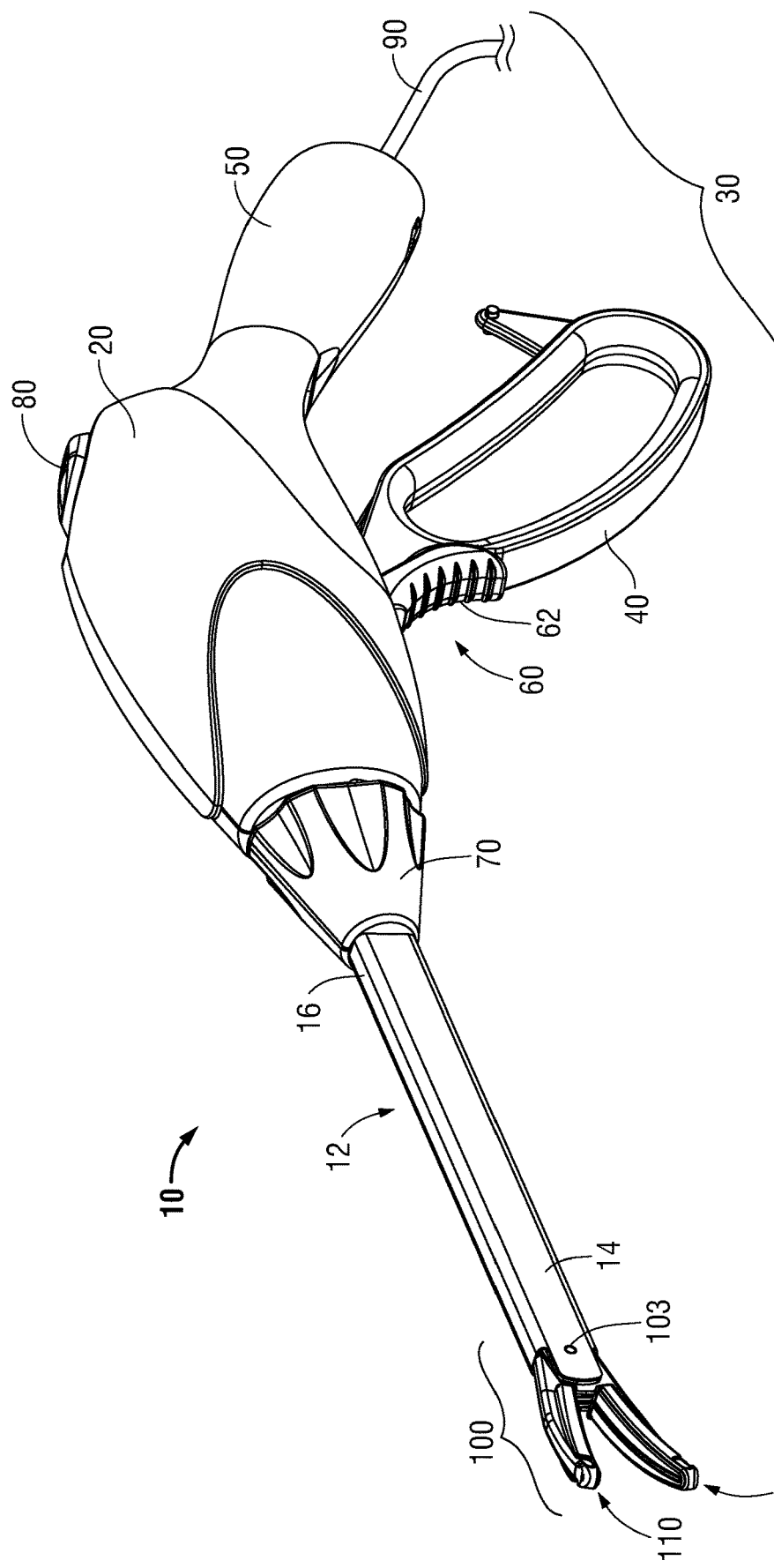
FIG. 1 is a perspective view of a shaft-based electrosurgical forceps provided in accordance with the present disclosure.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, an activation switch 80, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable 90 that connects forceps 10 to an energy source (not shown), e.g., an electrosurgical generator. Cable 90 includes a wire (or wires) (not shown) extending therethrough that has sufficient length to extend through shaft 12 in order to provide energy to one or both tissue-treating surfaces 114, 124 of jaw members 110, 120, respectively, of end effector assembly 100 (see FIGS. 2A and 2B). Activation switch 80 is coupled to tissue-treating surfaces 114, 124 (FIGS. 2A and 2B) and the source of energy for enabling the selective activation of the supply of energy to jaw members 110, 120 for treating, e.g., cauterizing, coagulating/desiccating, and/or sealing, tissue.

Handle assembly 30 of forceps 10 includes a fixed handle 50 and a movable handle Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position (FIG. 2A) and an approximated position (FIG. 2B) to grasp tissue between jaw members 110, 120. As shown in FIG. 1, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120 (FIG. 2B).

Trigger assembly 60 includes a trigger 62 coupled to housing 20 and movable relative thereto between an un-actuated position and an actuated position. Trigger 62 is operably coupled to a knife 64 (FIG. 2A), so as to actuate knife 64 (FIG. 2A) to cut tissue grasped between jaw members 110, 120 of end effector assembly 100 upon actuation of trigger 62. As an alternative to knife 64, other suitable mechanical, electrical, or electromechanical cutting mechanisms (stationary or movable) are also contemplated.

Figure 2A:
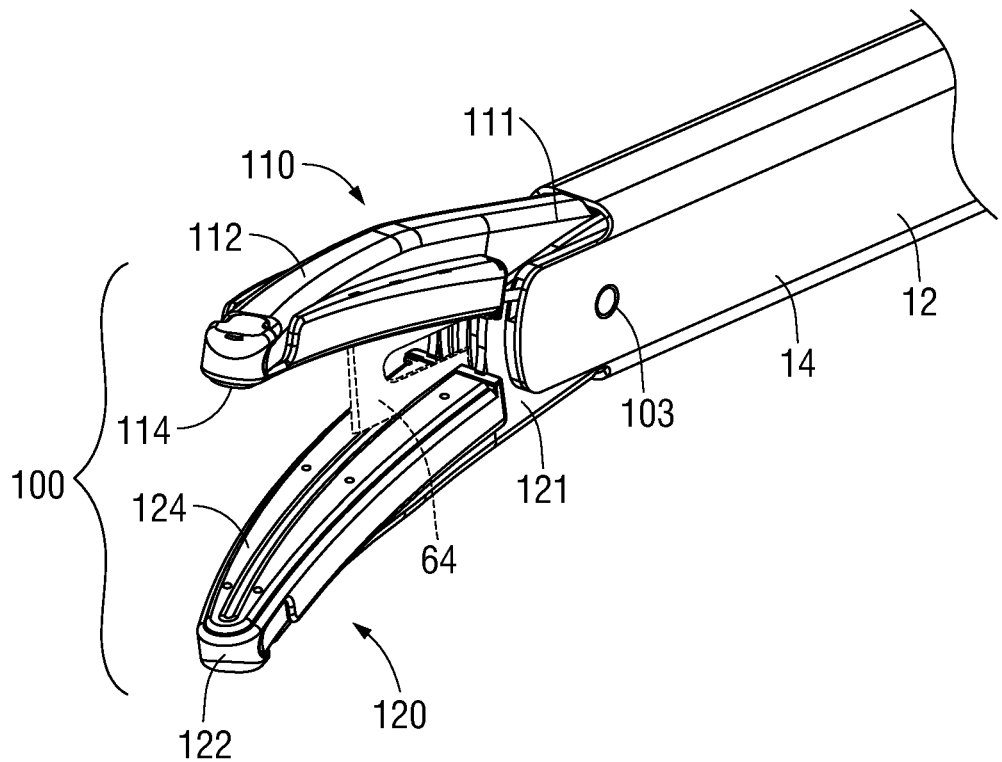
FIG. 2A is a perspective view of a distal end portion of the forceps of FIG. 1, wherein jaw members of an end effector assembly of the forceps are disposed in a spaced-apart position.
Figure 2B:
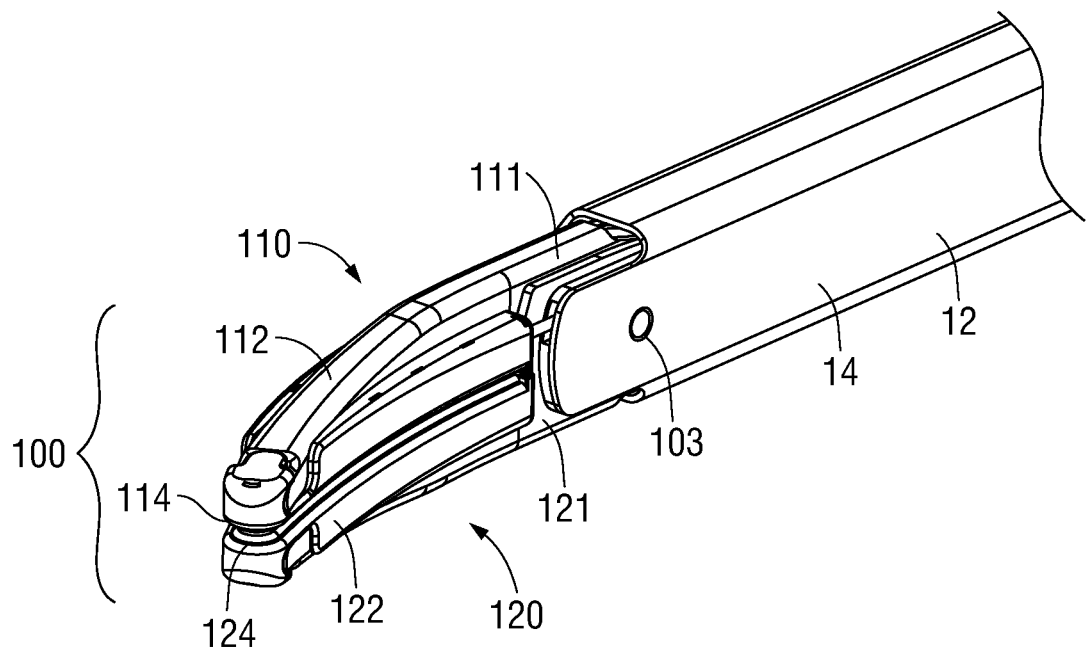
FIG. 2B is a perspective view of the distal end portion of the forceps of FIG. 1, wherein the jaw members are disposed in an approximated position.

With additional reference to FIGS. 2A and 2B, end effector assembly 100, as noted above, includes first and second jaw members 110, 120. Each jaw member 110, 120 includes a proximal flange portion 111, 121, an outer insulative jaw housing 112, 122 disposed about the distal portion (not explicitly shown) of each jaw member 110, 120, and a tissue-treating surface 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw members 110, 120 are configured to support jaw housings 112, 122, and tissue-treating surfaces 114, 124, respectively, thereon.

Outer insulative jaw housings 112, 122 of jaw members 110, 120 support and retain tissue-treating surfaces 114, 124 on respective jaw members 110, 120 in opposed relation relative to one another. Tissue-treating surfaces 114, 124 are formed from an electrically conductive material, e.g., for conducting electrical energy therebetween for treating tissue, although tissue-treating surfaces 114, 124 may alternatively be configured to conduct any suitable energy, e.g., thermal, microwave, light, ultrasonic, etc., through tissue grasped therebetween for energy-based tissue treatment. As mentioned above, tissue-treating surfaces 114, 124 are coupled to activation switch 80 and the source of energy (not shown), e.g., via the wires (not shown) extending from cable 90 through forceps 10, such that energy may be selectively supplied to tissue-treating surface 114 and/or tissue-treating surface 124 and conducted therebetween and through tissue disposed between jaw members 110, 120 to treat tissue.

Figure 3:
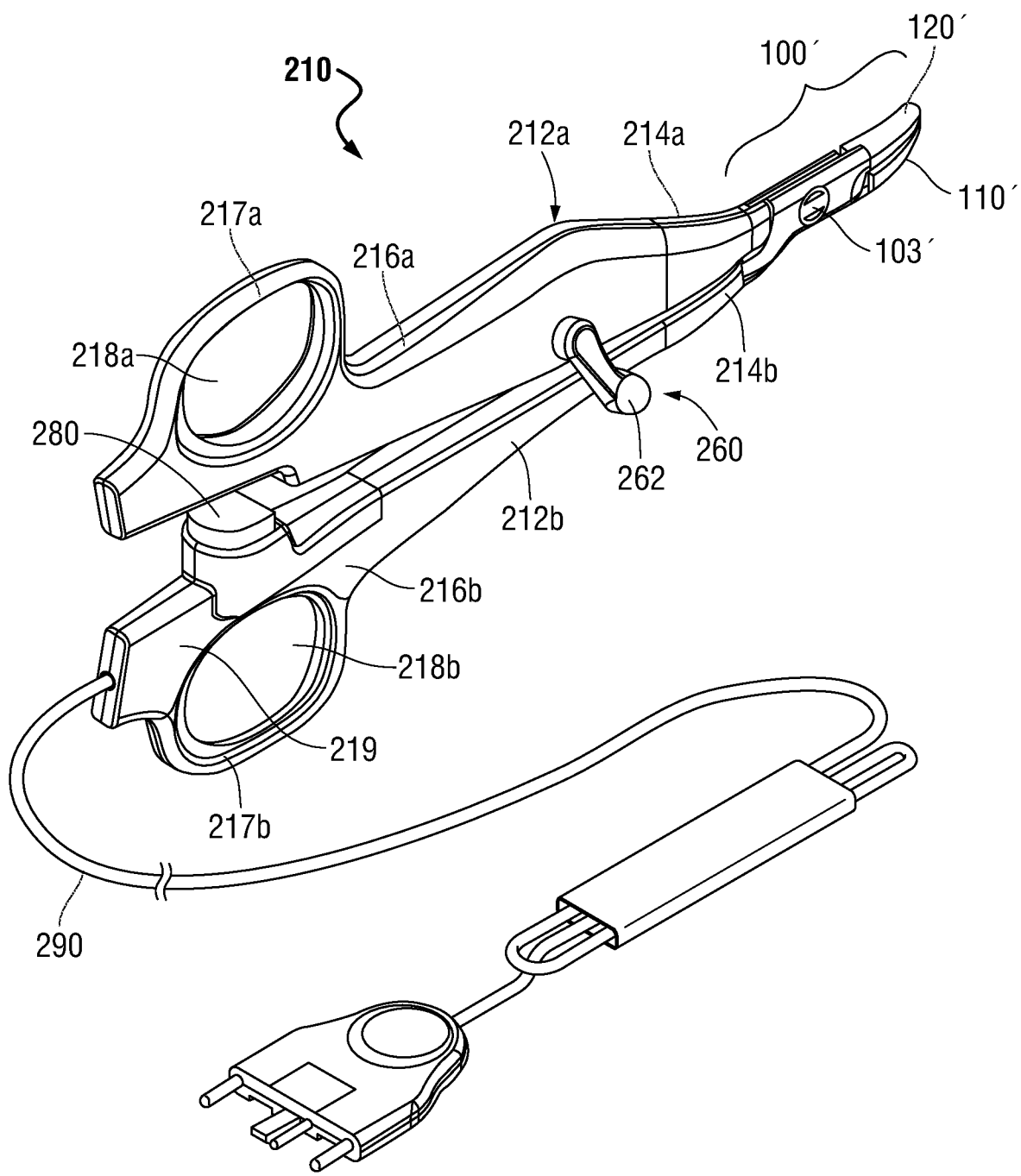
FIG. 3 is a perspective view of a hemostat-style electrosurgical forceps provided in accordance with the present disclosure.

Referring to FIG. 3, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Forceps 210 includes two elongated shaft members 212a, 212b, each having a proximal end portion 216a, 216b, and a distal end portion 214a, 214b, respectively. Forceps 210 is configured for use with an end effector assembly 100' similar to end effector assembly 100 (FIGS. 2A and 2B). More specifically, end effector assembly 100' includes first and second jaw members 110', 120' attached to respective distal end portions 214a, 214b of shaft members 212a, 212b. Jaw members 110', 120' are pivotably connected about a pivot 103'. Each shaft member 212a, 212b includes a handle 217a, 217b disposed at the proximal end portion 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212a, 212b of forceps 210, e.g., shaft member 212b, includes a proximal shaft connector 219 configured to connect forceps 210 to a source of energy (not shown), e.g., a generator. Proximal shaft connector 219 secures a cable 290 to forceps 210 such that the user may selectively supply energy to jaw members 110', 120' for treating tissue and for energy-based tissue cutting. More specifically, an activation switch 280 is provided for supplying energy to jaw members 110', 120' to treat tissue upon sufficient approximation of shaft members 212a, 212b, e.g., upon activation of activation switch 280 via shaft member 212a.

Forceps 210 further includes a trigger assembly 260 including a trigger 262 coupled to one of the shaft members, e.g., shaft member 212a, and movable relative thereto between an un-actuated position and an actuated position. Trigger 262 is operably coupled to a knife (not shown; similar to knife 64 (FIG. 2A) of forceps 10 (FIG. 1)) so as to actuate the knife to cut tissue grasped between jaw members 110,' 120' of end effector assembly 100' upon movement of trigger 262 to the actuated position. Similarly as noted above with respect to forceps 10 (FIG. 1), other suitable cutting mechanisms are also contemplated.

Figure 4:
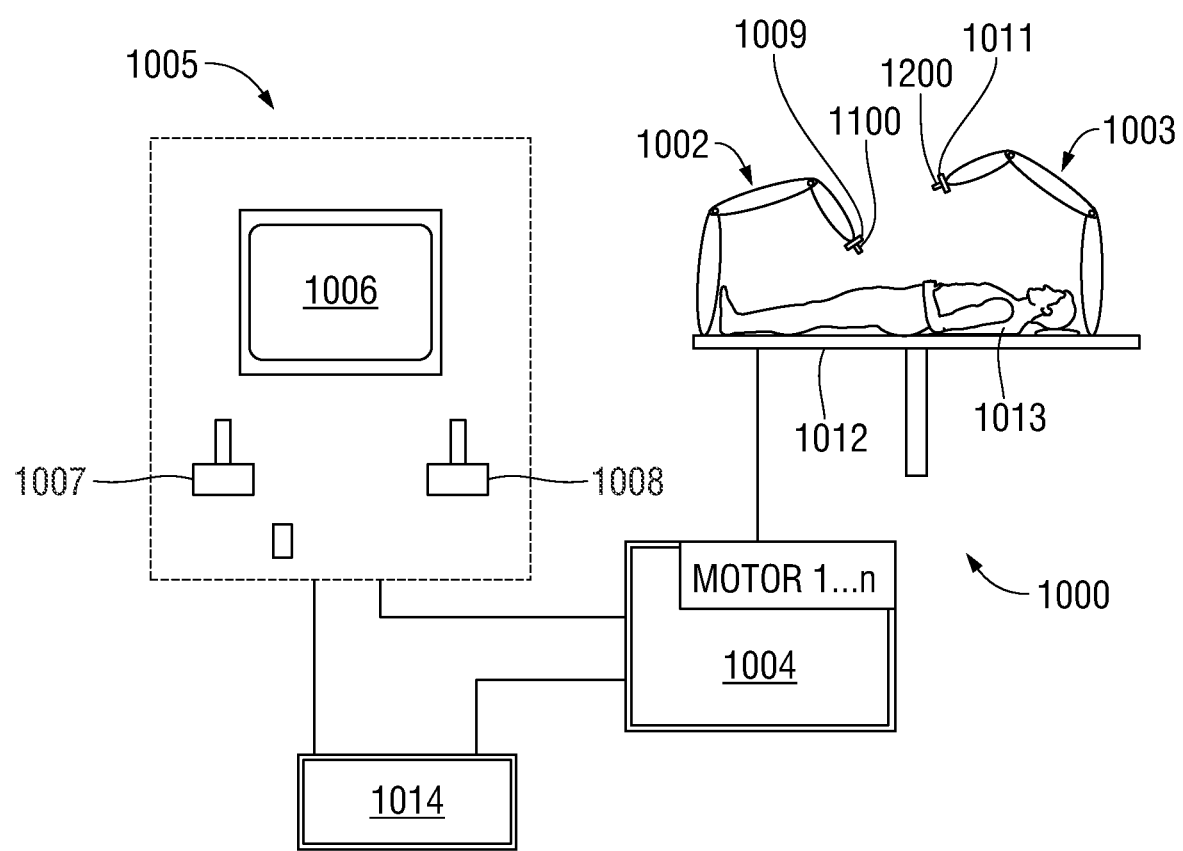
FIG. 4 is a schematic illustration of a robotic surgical instrument provided in accordance with the present disclosure.

Referring to FIG. 4, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical instrument 1000 may be configured for use on a patient 1013 lying on a patient table 1012 to be treated in a minimally invasive manner. Robotic surgical instrument 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to end effector assembly 100 (FIGS. 2A and 2B), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 5:
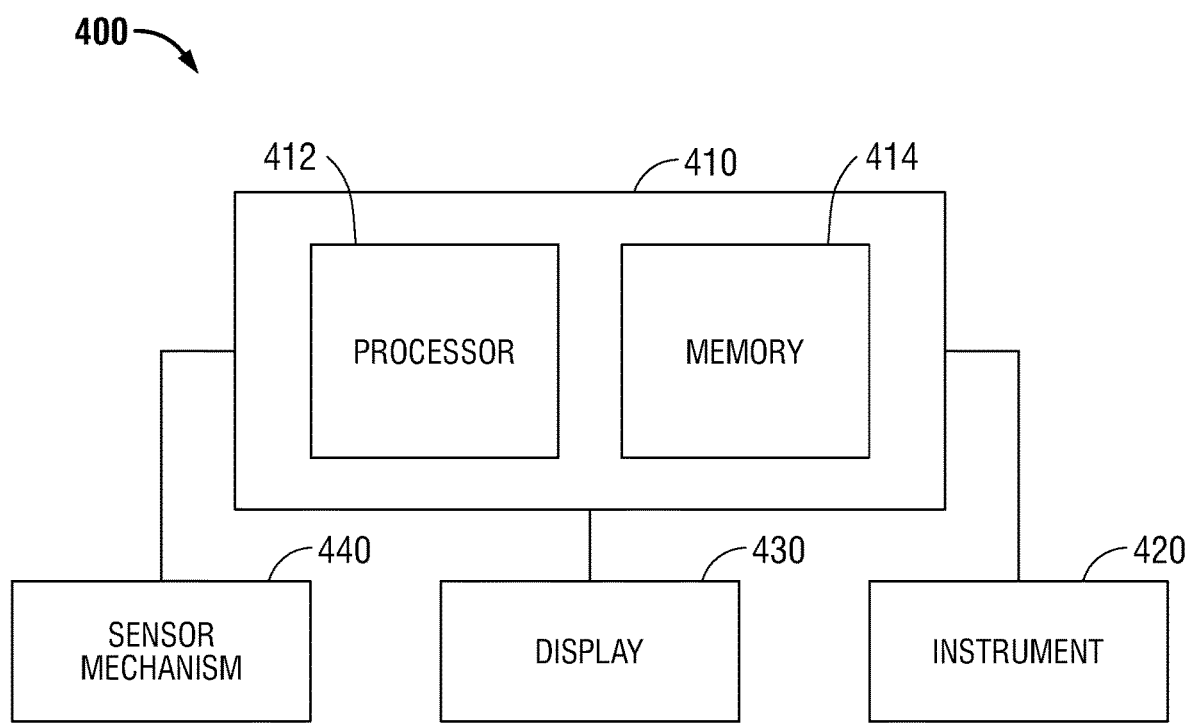
FIG. 5 is a block diagram of a surgical system provided in accordance with the present disclosure.
Figure 8:
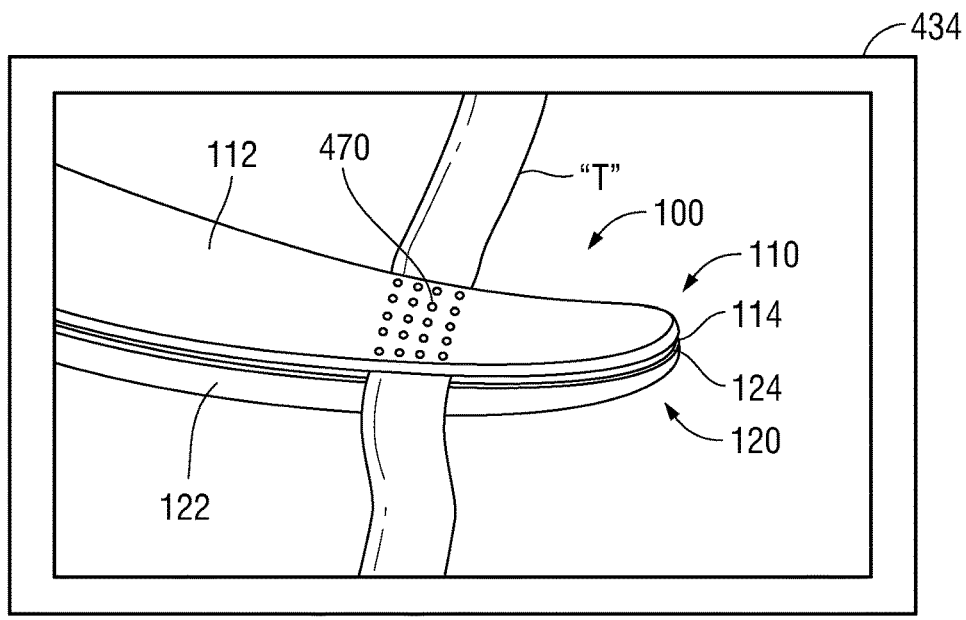
FIG. 8 is a front view of a surgical display displaying thereon the jaw members of the end effector assembly of FIGS. 2A and 2B grasping tissue therebetween, wherein the surgical display includes yet another tissue indication provided in accordance with the present disclosure.

Referring to FIG. 5, a surgical system provided in accordance with the present disclosure is shown generally identified by reference numeral 400. Surgical system 400 includes a controller 410 that has a processor 412 and a memory 414. Surgical system 400 also includes one or more surgical instruments 420, e.g., forceps 10 (FIG. 1), forceps 10' (FIG. 3), robotic surgical instrument 1000 (FIG. 4), and/or other suitable instrument(s), a display 430, and a sensor mechanism 440. Controller 410, in embodiments, is incorporated into the one or more surgical instruments 420, e.g., forceps 10 (FIG. 1), forceps 10' (FIG. 3), or robotic surgical system 1000 (FIG. 4), or may be separate therefrom, e.g., incorporated into the generator or a standalone component, and connected via wired or wireless connection, locally or remotely. Likewise, as detailed below, display 430 may be incorporated into the one or more surgical instruments 420, e.g., forceps 10 (FIG. 1), forceps 10' (FIG. 3), or robotic surgical system 1000 (FIG. 4), or may be separate, e.g., as a standalone surgical display 434 (FIG. 8). Further, sensor mechanism 440 may be incorporated into the one or more surgical instruments 420, e.g., forceps 10 (FIG. 1), forceps 10' (FIG. 3), or robotic surgical system 1000 (FIG. 4), or may be separate therefrom.

Controller 410 is configured to receive sensor data from sensor mechanism 440 and, based thereupon, generate a tissue indication that is output to display 430 for displaying the tissue indication to the user, as detailed with respect to the various embodiments described below, although other suitable configurations for displaying a tissue indication to the user are also contemplated. Additionally or alternatively, controller 410 is configured to receive sensor data from sensor mechanism 440, determine, and output other information relating to tissue independently of the tissue indication or in conjunction therewith. Such information may include the presence and/or location of tissue, a tissue type, a tissue state, the presence and/or location of a foreign object, the presence and/or location of a critical tissue, etc.

Figure 6:
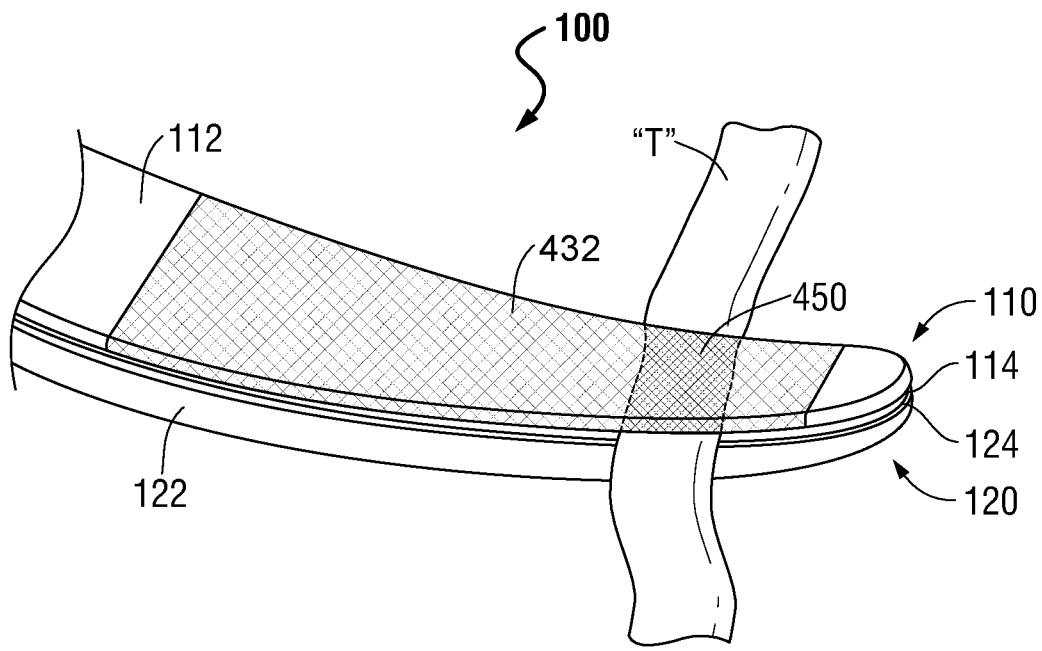
FIG. 6 is a perspective view of the jaw members of the end effector assembly of FIGS. 2A and 2B shown grasping tissue therebetween and including a tissue indication provided in accordance with the present disclosure.

Referring to FIG. 6, in conjunction with FIG. 5, in embodiments, one of the jaw members 110, 120 of end effector assembly 100, e.g., jaw member 110, may include display 430, in the form of an integrated display 432, disposed thereon. Integrated display 432 may include an LCD display, an OLED display, a plasma display, a LED display, or other suitable display. Integrated display 432 is positioned to be visible from an exterior-facing surface of outer insulative jaw housing 112 of jaw member 110. Integrated display 432 may extend along a portion or the entirety of the length of outer insulative jaw housing 112 and may be configured to display a tissue indication 450 in the form of a video image; visual effect (blinking lights, for example); contrast pattern, color, etc.; banner (including images, colors, patterns, and/or text); etc., providing a readily-identifiable tissue indication 450 to indicate to the user tissue "T," e.g., a vessel, grasped between the jaw members 110, 120. The tissue indication 450, more specifically, may indicate a location of the grasped tissue "T" along the length of jaw member 110, a size of the grasped tissue "T" relative to jaw member 110, and/or properties or features of the grasped tissue "T," e.g., tissue texture, tissue type, tissue state, etc. Knowing the location of the grasped tissue "T" along the length of jaw member 110, the size of the grasped tissue "T" relative to the jaw member 110, and/or properties or features of the grasped tissue "T" enables a user to determine, for example, whether the grasped tissue "T" is properly positioned between jaw members 110, 120 and/or whether the grasped tissue "T" is too larger or too small, thus allowing the user to determine, for example, whether re-grasping or other remedial action is necessary or whether the user can proceed to treat and/or cut the tissue "T." Such information also enables a user to determine whether the grasped tissue "T" is appropriate to be treated, e.g., sealed, and/or cut, and, further, what particular technique or techniques are to be used on the grasped tissue "T" to facilitate treating and/or cutting the grasped tissue "T."

In order to display tissue indication 450 on integrated display 432, controller 410 receives sensor data from sensor mechanism 440 and, based thereupon, generates an appropriate output that is provided to integrated display 432 for appropriately displaying tissue indication 450 thereon, e.g., turning on the appropriate portions of integrated display 432 to provide a map on outer insulative housing 112 of jaw member 110 of the location and relative size of tissue "T" grasped between jaw members 110, 120

Figure 7:
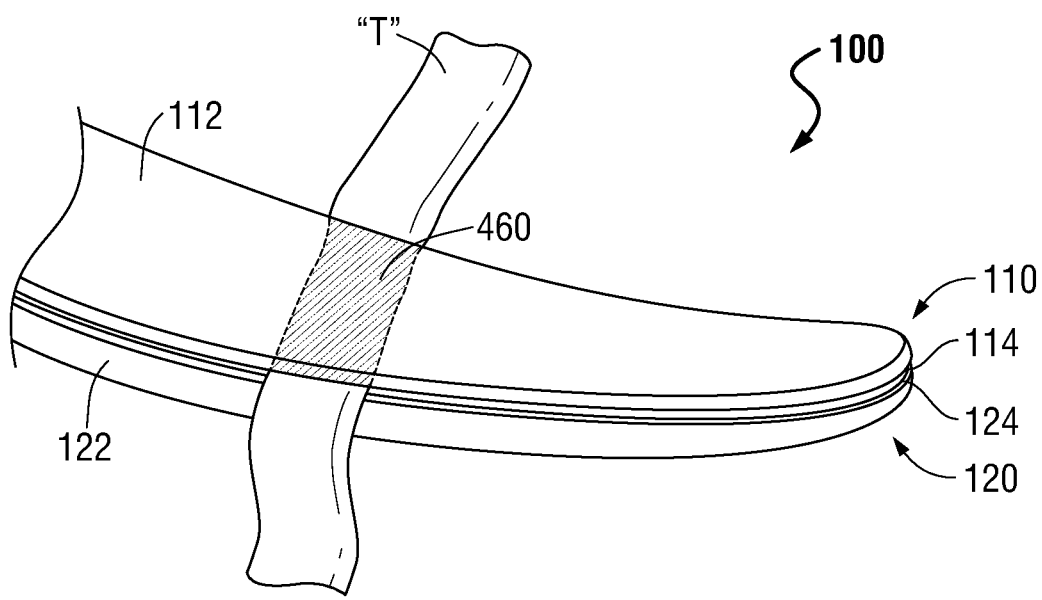
FIG. 7 is a perspective view of the jaw members of the end effector assembly of FIGS. 2A and 2B shown grasping tissue therebetween and including another tissue indication provided in accordance with the present disclosure.

Referring to FIG. 7, in conjunction with FIG. 5, as an alternative to an integrated display 432 disposed on jaw member 110 (see FIG. 6), display 430 may take the form of a virtual display configured to project a tissue indication 460 onto outer insulative jaw housing 112 of jaw member 110 (or onto another suitable portion of end effector assembly 100). With respect to a virtual display configuration, display 430, in communication with controller 410, is configured to project the tissue indication 460 in the form of a video image; visual effect (blinking lights, for example); contrast pattern, color, etc.; banner (including images, colors, patterns, and/or text); etc., providing a readily-identifiable tissue indication 460, similarly as detailed above with respect to tissue indication 450.

In order to display tissue indication 460, controller 410 receives sensor data from sensor mechanism 440 and, based thereupon, generates an appropriate output that is provided to display 430 for projecting the virtual tissue indication 460 onto jaw member 110. It is noted that projecting the virtual tissue indication 460 onto jaw member 110 does not require physical projection of light (or other signal) onto jaw member 110 but, rather, includes projection in a manner that appears to the user as if the virtual tissue indication 460 is disposed on jaw member 110. For example, display 430 may include an augmented reality headset (not shown) that projects the virtual tissue indication 460 onto a lens (or lenses) of the augmented reality headset such that it appears to the user wearing the headset that the virtual tissue indication 460 is disposed on jaw member 110.

With reference to FIG. 8, as opposed to displaying the tissue indication 450, 460 (FIGS. 6 and 7) on jaw member 110 (physically or virtually), the display 430 may include a surgical display 434 onto which the tissue indication 470 is overlaid. More specifically, the surgical display 434 may be configured to display a video image of the surgical site, e.g., from an endoscope (not shown) disposed at the surgical site, and to overlay the tissue indication 470 onto a portion of the displayed image, e.g., onto the portion of the image representing outer insulative jaw housing 112 of jaw member 110. As such, when viewing surgical display 434, it appears to the user as though the tissue indication 470 is disposed on jaw member 110. The tissue indication 470 may be in the form of a video image; visual effect (blinking lights, for example); contrast pattern, color, etc.; banner (including images, colors, patterns, and/or text); etc., providing a readily-identifiable tissue indication 470 similarly as detailed above.

In order to display tissue indication 470 on surgical display 434, controller 410 receives sensor data from sensor mechanism 440 and, based thereupon, generates an appropriate output that is provided to surgical display 434 for overlaying tissue indication 470 onto jaw member 110.

Figure 9:
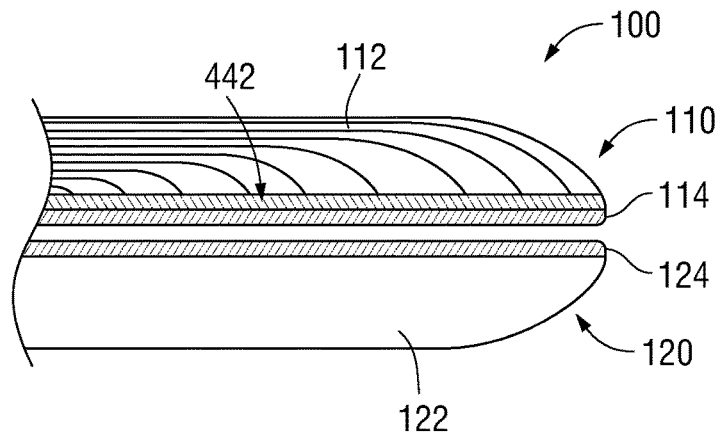
FIG. 9 is a longitudinal, cross-sectional view of the jaw members of the end effector assembly of FIGS. 2A and 2B including a sensor mechanism provided in accordance with the present disclosure.

Turning to FIG. 9, in conjunction with FIG. 5, as noted above, in order to display a tissue indication, controller 410 receives sensor data from sensor mechanism 440 and, based thereupon, generates an appropriate output that is provided to display 430 for displaying the tissue indication. In embodiments, sensor mechanism 440 may include one or more pressure-sensitive resistive panels 442 incorporated into jaw member 110. More specifically, the one or more pressure-sensitive resistive panels 442 may be disposed underneath at least a portion of tissue-treating surface 114 of jaw member 110, on top of at least a portion of tissue-treating surface 114, may form part of tissue-treating surface 114, may surround a portion of the perimeter (e.g., the longitudinal portions of the perimeter) of tissue-treating surface 114, and/or may be disposed in any other suitable manner relative to tissue-treating surface 114 and jaw member 110. Alternatively or additionally, one or more pressure-sensitive resistive panels 442 may be disposed on jaw member 120 (associated with tissue-treating surface 124 or in any other suitable manner).

The one or more pressure sensitive-resistor panels 442 is configured to sense a force acting thereon and a location(s) of the applied force. In this manner, controller 410, using the force and location data provided by the one or more pressure-sensitive resistor panels 442 can determine the location(s) along jaw member 110 where tissue is grasped (as the grasped tissue provides the applied force) and the location(s) along jaw member 110 where no tissue is grasped (where no applied force is detected or where a detected applied force is below a minimum threshold). The resulting pressure map of jaw member 110 can then be converted to a visual map that is output as a tissue indication for display on display 430. The resulting pressures and/or pressure map detected may additionally or alternatively be communicated to, for example, the generator for use in controlling the supply of energy to jaw members 110, 120 for treating, e.g., cauterizing, coagulating/desiccating, and/or sealing, tissue.

As an alternative to pressure-sensitive resistor panels 442, other suitable mapping panels configured to determine the location of tissue grasped between jaw members 110, 120 are also contemplated such as, for example, one or more capacitive touch panels.

Figure 10:
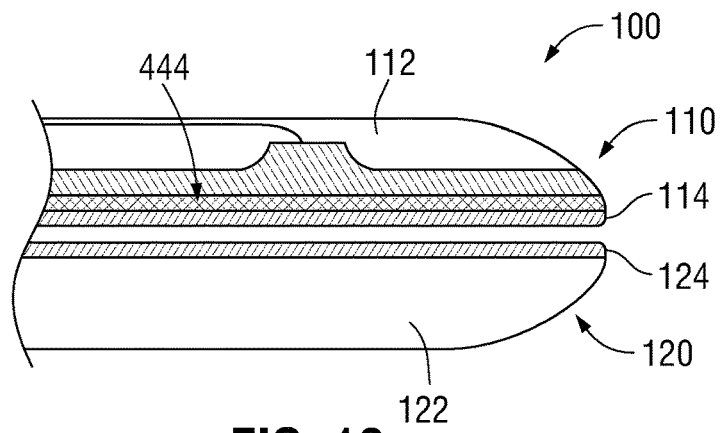
FIG. 10 is a longitudinal, cross-sectional of the jaw members of the end effector assembly of FIGS. 2A and 2B including another sensor mechanism provided in accordance with the present disclosure.

Referring to FIG. 10, in embodiments, sensor mechanism 440 may include an elastomeric contact sensor 444 disposed on top of at least a portion of tissue-treating surface 114, forming part of tissue-treating surface 114, surrounding the perimeter (or at least the longitudinal portions of the perimeter) of tissue-treating surface 114, and/or disposed in any other suitable manner relative to tissue-treating surface 114 and jaw member 110 and/or tissue-treating surface 124 and jaw member 120.

Elastomeric contact sensor 444 is configured to conform to the topography of material, e.g., tissue, in contact therewith, thus indicating the presence of tissue along jaw member 110, the location of tissue along jaw member 110, and, further, the texture of tissue grasped between jaw members 110, 120. The presence and location information may be used similarly as detailed above, e.g., converted to a visual map that is output as a tissue indication for display on display 430. The texture information may likewise be utilized in generating the tissue indication, e.g., providing as part of the tissue indication a visual image or other indication of the texture of the grasped tissue. The texture information may additionally or alternatively be communicated to, for example, the generator for use in controlling the supply of energy to jaw members 110, 120 for treating, e.g., cauterizing, coagulating/desiccating, and/or sealing, tissue.

The texture information may alternatively or additionally be utilized to determine properties and/or features of the grasped tissue as part of the tissue indication or separate therefrom (without or without the tissue indication). For example, as different tissue types (muscle, vascular, non-vascular, organ, etc.) and/or different tissue states (diseased, inflamed, calcified, etc.) have different textures, controller 410 may be configured to associate a tissue type and/or tissue state with the texture information and indicate the same via the tissue indication or separately therefrom. In such embodiments, a look-up table, algorithm, and/or artificial intelligence program (e.g., stored within memory 414) may be utilized to associate the tissue type and/or tissue state with the texture information. The one or more properties and/or features determined form the texture information may additionally or alternatively be communicated to, for example, the generator for use in controlling the supply of energy to jaw members 110, 120 for treating, e.g., cauterizing, coagulating/desiccating, and/or sealing, tissue.

As another example, the texture sensed by elastomeric contact sensor 444 may be utilized to determine the presence of non-tissue objects, e.g., surgical objects such as tubes, sutures, other instruments, implants, etc., and/or critical tissues to avoid such as organs, nerves, etc. When a non-tissue object and/or critical tissue is detected, a warning may be incorporated into the tissue indication or may be provided separately therefrom.

In addition or as an alternative to determining and displaying a tissue indication based on sensed data regarding tissue (or non-tissue objects), as detailed below, the sensed data may be utilized to create haptic feedback at one or more haptic devices disposed at user control(s), e.g., to mimics the location, texture, compressibility, etc. of tissue as the end effector interfaces with tissue, thus facilitating a surgeon's "feel" in minimally invasive, robotic, and other surgical procedures where natural "feel" is reduced or eliminated.

It should be understood that various aspects disclosed herein may be combined in different combinations than the combinations specifically presented hereinabove and in the accompanying drawings. In addition, while certain aspects of the present disclosure are described as being performed by a single module or unit for purposes of clarity, it should be understood that the techniques of this disclosure may be performed by a combination of units or modules associated with, for example, a surgical system.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structures or any other physical structure suitable for implementation of the described techniques. Also, the techniques could be fully implemented in one or more circuits or logic elements.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
an end effector assembly including first and second jaw members each defining a tissue-treating surface, at least one of the first or second jaw members movable relative to the other between a spaced-apart position and an approximated position for grasping tissue between the tissue-treating surfaces thereof, at least one of the first or second jaw members including a sensor;
a display; and
a controller configured to receive sensor data from the sensor, generate a tissue indication based upon the sensor data, and output the tissue indication to the display, the display configured to display, on the end effector assembly, the tissue indication generated based upon the sensor data, wherein the tissue indication indicates a location along the first jaw member at which tissue is grasped between the tissue-treating surfaces of the first and second jaw members.

2. The electrosurgical system according to claim 1, wherein the display is an integrated display incorporated into the first jaw member and viewable from an exterior-facing surface thereof, and
wherein the tissue indication is display on the integrated display.

3. The electrosurgical system according to claim 1, wherein the display is configured to project the tissue indication, virtually, onto an exterior-facing surface of the first jaw member.

4. The electrosurgical system according to claim 1, wherein the display is a surgical display configured to display a video image of a surgical site, and wherein the display is configured to overlay the tissue indication, virtually, on an image of an exterior-facing surface of the first jaw member displayed on the surgical display.

5. The electrosurgical system according to claim 1, wherein the tissue indication is further configured to indicate a size of tissue grasped between the tissue-treating surfaces of the first and second jaw members relative to a size of the first jaw member.

6. The electrosurgical system according to claim 1, wherein the sensor includes at least one pressure-sensitive resistive panel.

7. The electrosurgical instrument according to claim 1, wherein the sensor includes an elastomeric contact sensor.

8. The electrosurgical instrument according to claim 1, further comprising:
a housing; and
a shaft extending distally from the housing, wherein the end effector assembly is disposed at a distal end portion of the shaft.

9. The electrosurgical instrument according to claim 8, further comprising a manual actuator coupled to the housing and configured to move the at least one of the first or second jaw members between the spaced-apart position and the approximated position.

10. The electrosurgical instrument according to claim 1, further comprising:
first and second shaft members pivotably coupled to one another about a pivot, wherein the end effector assembly extends distally from the pivot, and wherein the first and second shaft members are movable relative to one another to move the at least one of the first or second jaw members between the spaced-apart position and the approximated position.

11. The electrosurgical instrument according to claim 1, further comprising:
a robotic arm, wherein the end effector assembly extends distally from the robotic arm.

12. The electrosurgical instrument according to claim 1, wherein the tissue indication is visually perceptible on the end effector assembly when an electrical signal generated based upon the sensor data is transmitted to the end effector assembly such that the electrical signal causes the tissue indication to be displayed on the end effector assembly.

13. The electrosurgical system according to claim 1, further comprising a processor and a a memory having instructions stored thereon, which when executed by the processor, cause the tissue indication to be displayed on an exterior-facing surface of the end effector assembly.

14. An electrosurgical system, comprising:
an end effector assembly including first and second jaw members each defining a tissue-treating surface, at least one of the first or second jaw members movable relative to the other between a spaced-apart position and an approximated position for grasping tissue between the tissue-treating surfaces thereof, at least one of the first or second jaw members including a contact sensor; and
a controller configured to receive sensor data from the contact sensor indicating a texture of tissue grasped between the first and second jaw members, the controller configured to determine at least one of a type of tissue, a state of tissue, or the presence of a foreign object or a critical tissue based upon the sensor data, the controller configured to display, on the end effector assembly, a determination, based upon the sensor data, of at least one of a type of tissue, a state of tissue, or the presence of a foreign object or a critical tissue.

15. The electrosurgical instrument according to claim 14, wherein the contact sensor is an elastomeric contact sensor.

16. The electrosurgical instrument according to claim 14, further comprising:
a housing; and
a shaft extending distally from the housing, wherein the end effector assembly is disposed at a distal end portion of the shaft.

17. The electrosurgical instrument according to claim 16, further comprising a manual actuator coupled to the housing and configured to move the at least one of the first or second jaw members between the spaced-apart position and the approximated position.

18. The electrosurgical instrument according to claim 14, further comprising:
first and second shaft members pivotably coupled to one another about a pivot, wherein the end effector assembly extends distally from the pivot, and wherein the first and second shaft members are movable relative to one another to move the at least one of the first or second jaw members between the spaced-apart position and the approximated position.

19. The electrosurgical instrument according to claim 14, further comprising:
a robotic arm, wherein the end effector assembly extends distally from the robotic arm.

20. The electrosurgical instrument according to claim 14, further comprising:
a display,
wherein the controller is further configured to generate a tissue indication based upon the sensor data, and output the tissue indication to the display, the display configured to display the tissue indication.

\* \* \* \* \*